United States Patent [19]

Holtkamp

[11] Plant 5,022

[45] Apr. 5, 1983

[54] AFRICAN VIOLET PLANT

[76] Inventor: Reinhold Holtkamp, Werther Strasse 112, 4294 Isselburg, Fed. Rep. of Germany

[21] Appl. No.: 300,556

[22] Filed: Sep. 9, 1981

[51] Int. Cl.[3] ..... A01H 5/00
[52] U.S. Cl. ..... Plt./69
[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new cultivar of African violet known by the cultivar name Wyoming characterized by its strong and sturdy flower stems which are tilted slightly sidewards forming a loose flower head, with the blossoms being blue-violet in color, and the center of the blossoms being relatively darker, velvety and shiny. The plant is uniform in growth and has a profuse corolla of essentially continuously blooming flowers which are non-dropping and long-lasting.

1 Drawing Figure

The present invention comprises a new and distinct cultivar of African violet plant, botanically known as *Saintpaulia ionantha,* and hereinafter referred to by the cultivar name Wyoming.

The new cultivar was referred to during the breeding and selection process by the designation d 198/5, and is a product of a planned breeding program. The basic objective of the breeding program was to create a new African violet cultivar having a compact growth habit with an upright and compact corolla of blue to blue-violet blossoms.

The new cultivar was originated from a cross made in a controlled breeding program in Isselburg, West Germany. The female, or seed parent was a cultivar designated 26 BI blue. The male, or pollen parent was a cultivar designated b 36/1 blue frilled.

The new cultivar Wyoming was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Wyoming has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Wyoming, which in combination distinguish this African violet as a new and distinct cultivar:

1. Compact growth with small leaves.
2. Upright, strong and sturdy flower stems, slightly tilted sidewards, forming a loose flower head.
3. Nine or more flower stems blooming continuously, with nine or more flowers per stem.
4. Center of flower is dark, velvety and shiny.
5. Uniform in growth, producing a profuse corolla.

6. Attractive saleable plant with compact flower head within 7–8 weeks after potting.
7. Blue-violet flower color.
8. Blooms almost continuously, with non-dropping and long lasting blossoms.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Wyoming.

Parentage:

*Male parent.*—b 36/1 blue frilled.

*Female parent.*—26 BI blue.

Propagation: The new cultivar holds its distinguishing characteristics through successive propagations by leaf cuttings and by division of shoots.

Plant: From 7 cm. to 9 cm. tall when grown in pots, and approximately 25 cm. in diameter when fully grown.

Leaves:

*General form.*—Heart-shaped, small.

*Diameter.*—45–50 mm.

*Texture.*—Leathered, slightly hairy.

*Aspect.*—Shiny.

*Veins.*—Upperside slightly visible; underside well-pronounced, light green, shiny and hairy.

*Color (upperside).*—HCC spinach green 0960.

*Color (underside).*—HCC willow green 000862/3.

*Petiole.*—Young petiole brownish green, hairy, underside with green tinge; old petiole slightly lighter.

Flowers:

*Bud.*—Ball-shaped, 8 mm. just before opening; 6–9 or more per stem.

*Sepals.*—Color: Greenish brown. Calyx: Funneled. Aspect: Spear-shaped, hairy. Peduncle: Strong, upright above leaves; greenish brown, hairy.

Individual flowers:

*Size.*—30–40 mm.

*Color.*—Upperside: Victoria violet 738, center a tone deeper. Underside: Victoria violet 738/3. Borne: Flower carries 6–9 or more flowers on short strong peduncles; flowers occasionally display an additional small petal in center of blossom, even up to 7 petals.

*Shape.*—Conventional (2 small and 3 larger petals).

*Corolla.*—Tilted flower stems produce a profuse but relatively loose corolla.

*Flowering time.*—First flowers appear 7–8 weeks after potting; after 9–10 weeks full flowering saleable plant is ready.

Reproductive organs:

*Stamens.*—2 anthers, composed of 2 cells, with seed capsule pushed slightly through.

*Anthers.*—HCC Dresden yellow 64.

*Filaments.*—3 mm. long; yellowish green with partly purple.

*Styles.*—7 mm. amethyst violet 35; base of ovary light green and hairy.

*Pollen color.*—HCC Dresden yellow 64/3.

Roots: White when young and active; greenish brown when older; normally developed.

Disease resistance: Good as experienced to date.

General observations: Wyoming is a compact growing variety with many small leaves and a profuse flowering, loose corolla. Blooming is almost continuous, with the more mature flowers tilting sidewards making room for fresh new flower stems in the center. Mature flowers don't fade; they slowly dry off. Its flowers are non-dropping and long-lasting.

I claim:

1. A new and distinct cultivar of African violet known by the cultivar Wyoming and particularly characterized by the combined features of compact growth habit with relatively small leaves; upright, strong and sturdy stems which tilt slightly sidewards, forming a profuse, loose flower head; 9 or more flower stems, with 9 or more blue and continuously blooming flowers appearing on each stem, with the center of each flower being relatively darker, velvety and shiny; uniform growth habit; attractive saleable plant with compact flower head within 7–8 weeks after potting, and by its non-dropping and long lasting blossoms.

* * * * *

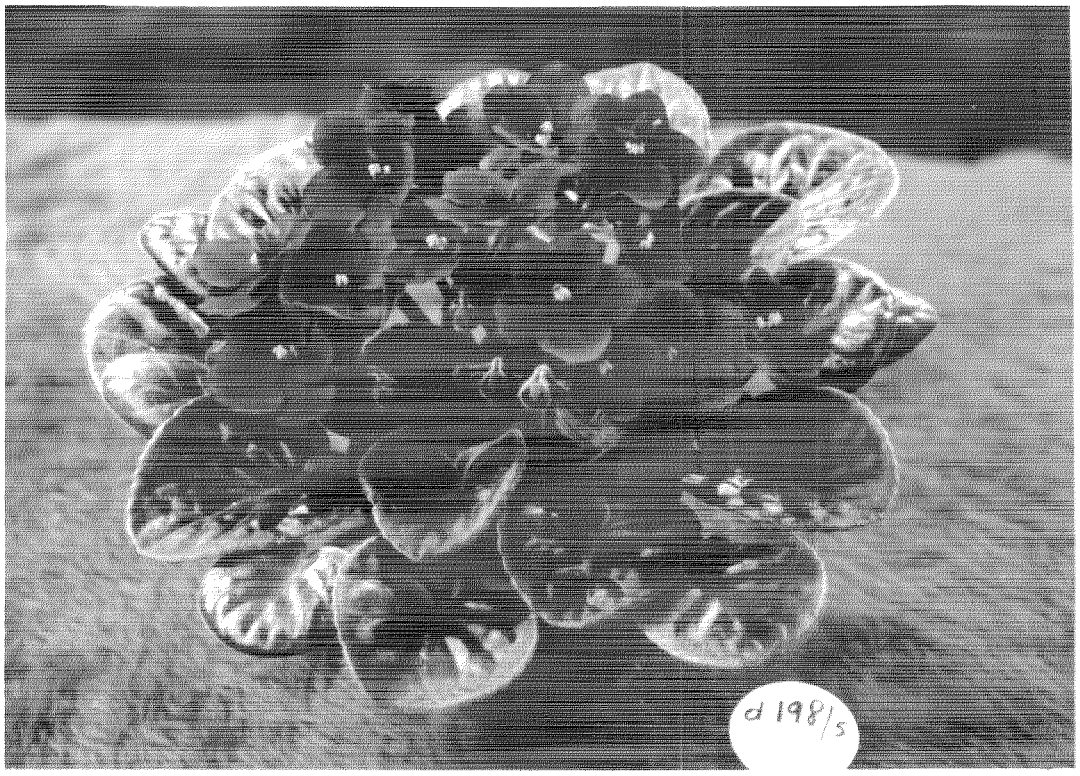
d 198/5